United States Patent [19]

Mas et al.

[11] Patent Number: 5,241,086

[45] Date of Patent: Aug. 31, 1993

[54] PROCESS FOR THE PREPARATION OF BROMINATED COMPOUNDS, ESPECIALLY FROM ALCOHOLS

[75] Inventors: Jean-Manuel Mas, Villeurbanne; Pascal Metivier, Lyon, both of France

[73] Assignee: Rhone-Poulenc Chimie, Courbevoie, France

[21] Appl. No.: 985,756

[22] Filed: Dec. 4, 1992

Related U.S. Application Data

[63] Continuation of Ser. No. 849,837, Mar. 12, 1992, abandoned, which is a continuation of Ser. No. 632,666, Dec. 27, 1990, abandoned, which is a continuation of Ser. No. 365,977, Jun. 13, 1989, abandoned.

[30] Foreign Application Priority Data

May 2, 1989 [FR] France ................................ 89 05811

[51] Int. Cl.$^5$ .................... C07D 309/02; C07C 52/45
[52] U.S. Cl. ................................ 549/428; 549/434; 549/504; 558/61; 558/140; 560/226; 562/603; 570/258; 570/261; 570/206
[58] Field of Search ............. 549/428, 434, 504; 558/61, 140; 560/226; 562/603; 568/663; 570/258, 261, 206

[56] References Cited

U.S. PATENT DOCUMENTS 3,130,222  4/1964  Asadorian et al. ................. 562/603

FOREIGN PATENT DOCUMENTS 2082174  3/1982  United Kingdom ............... 562/603

OTHER PUBLICATIONS

Jean-Manuel MAS et al., "A New Simple and Industrial PRocess for Bromination of Alcohols", Synthetic Comunications, 22 (15) 2187–2191 (1992).
CA:97(14)114572W, Chem. Eng. News, vol. 60, No. 28, p. 5, 1982, "Caution With Thionyl Chloride".

*Primary Examiner*—Nicky Chan
*Attorney, Agent, or Firm*—Finnegan, Henderson, Farabow, Garrett & Dunner

[57] ABSTRACT

A process for the preparation of a brominated compound which comprises the step of reacting at least one compound selected from the group consisting of a chloroformate, a chlorosulfite and a chlorophosphite with a brominating agent for a time sufficient to obtain at least one brominated compound. In particular, an alcohol is converted into a chloroformate, chlorosulfite or a chlorophosphite, which is then brominated to obtain the desired product. In another embodiment, a brominating agent is reacted with a reactant selected from the group consisting of thionyl chloride, phosgene and phosphorous oxychloride, followed by contacting the reaction product obtained with an alcohol to be brominated.

15 Claims, No Drawings

PROCESS FOR THE PREPARATION OF BROMINATED COMPOUNDS, ESPECIALLY FROM ALCOHOLS

This application is a continuation of application Ser. No. 07/849,837, filed Mar. 12, 1992, now abandoned, which is a continuation of application Ser. No. 07/632,666, filed Dec. 27, 1990, abandoned, which is a continuation of application Ser. No. 07/365,977, filed Jun. 13, 1989, abandoned.

The present invention relates to the preparation of brominated compounds and more particularly the bromination of alcohols.

Brominated compounds are products of interest to industry, especially as synthesis intermediates, plant protection agents or insecticides.

Many processes for the bromination of alcohols are known which employ various brominating reactants such as hydrobromic acid, $SOBr_2$, $PBr_3$, or the combination of triphenylphosphine and bromine.

Disadvantageously, these prior processes are frequently non-industrial and have a mediocre yield or the processes employ costly or hazardous reactants.

In the particular case of the synthesis of 2-bromomethyltetrahydropyran, a product which can be employed as a nematicide, for example, the use of hydrobromic acid gives only poor yields because of the fragility of the ring in an acidic medium. Use of triphenylphosphine dibromide as the reactant is an improvement but, bearing in mind the price of triphenylphosphine dibromide, this is a process which is too expensive to be used industrially.

A first object of the invention is therefore a process which is relatively inexpensive but can produce a high yield of brominated compounds.

A second object of the invention is a process for the bromination of alcohols which is relatively inexpensive but can produce a high yield.

To this end, the process according to the invention broadly relates to the preparation of a brominated compound wherein a chloroformate, chlorosulfite or chlorophosphite compound is reacted with a brominating agent.

According to a particularly preferred embodiment, the process of the invention applies to the bromination of an alcohol, and comprises the following steps:

an alcohol is brought into contact with at least one reactant selected from thionyl chloride ($SOCl_2$), phosgene ($COCl_2$) and phosphorus oxychloride ($POCl_3$) to form at least one reaction product selected from a chloroformate, a chlorosulfite and a chlorophosphite; and the at least one reaction product resulting from the preceding stage is brought into contact with a brominating agent.

The process of the invention also relates to a process for bromination of a compound, such as an alcohol, which comprises the steps of first reacting a brominating agent with a reactant chosen from thionyl chloride, phosgene and phosphorus oxychloride, and secondly, the reaction mixture or the reaction product thus obtained is brought into contact with the compound, such as the alcohol, to be brominated.

By virtue of the process of the invention, yields are obtained which can go up to more than 90% in certain cases, even with industrial reactants.

Other details and characteristics of the invention will appear more clearly on reading the description and the examples which are to follow, no limitation being implied.

In the process of the invention, one either starts with or obtains as an intermediate a chloroformate, a chlorosulfite or a chlorophosphite compound, which compound is then brominated. As defined herein, the term chlorophosphite covers the monochlorophosphite and the dichlorophosphite.

In the case of a preferred embodiment of the invention where the process is applied to the bromination of an alcohol, the starting material is the alcohol corresponding to the brominated compound which it is desired to obtain. The above-mentioned chloroformate, chlorosulfite or chlorophosphite is prepared in a first stage by bringing the alcohol into contact with at least one of phosgene, thinyl chloride or phosphorus oxychloride.

Once the chloroformate, chlorosulfite or chlorophosphite derivative has been obtained, the product obtained can, in a second stage, be brought into contact or reacted with a brominating agent in the manner described above. It is therefore to be understood for the remainder of the description that the combination of the features described in the case of the subsequent stages applies integrally and identically t both the broader process and a preferred process relating to bromination of an alcohol.

The process of the invention applies to the preparation of a wide type of brominated compounds, especially by starting from primary or secondary alcohols. More particularly, the starting materials may be alcohols of formula (1)

$$\begin{array}{c} R_1 \\ \phantom{R_1}\diagdown \\ \phantom{R_1R_1}CHOH \\ \phantom{R_1}\diagup \\ R_2 \end{array} \quad (1)$$

in which $R_1$ and $R_2$ may be identical or different and are selected from the group consisting of a heterocyclic ring containing at least one heteroatom selected from oxygen, sulfur and nitrogen, a hydrogen atom, an alkyl, alkenyl or alkynyl radical, it being possible for these alkyl, alkenyl and alkynyl radicals to be linear or branched, a cycloalkyl, alkylcycloalkyl, terpene, $-CO_2R_3$, $-(CH_2)_n-CO_2R_3$, $-COR_3$, $-SOR_3$ or $SO_2R_3$ radical, n being an integer, and $R_3$ being selected from the group consisting of a hydrogen atom or an alkyl, alkenyl or alkynyl radical, it being possible for these alkyl, alkenyl and alkynyl radicals to be linear or branched, and an aryl, especially a substituted aryl, radical.

Preferably, n varies from 1 to 8 and more preferably from 1 to 4.

Thus, in particular, brominated compounds of formula (2),

$$\begin{array}{c} R_1 \\ \phantom{R_1}\diagdown \\ \phantom{R_1R_1}CHBr \\ \phantom{R_1}\diagup \\ R_2 \end{array} \quad (2)$$

in which $R_1$ and $R_2$ are as defined in formula (1), can be obtained using the process of the invention.

Rather than start from an alcohol, it is also possible to start from the corresponding chloroformates, chlorosulfites and chlorophosphites, that is to say from at least one product of formulae (3), (4), (5) and (6):

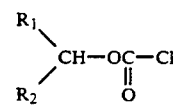 (3)

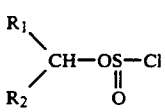 (4)

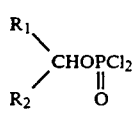 (5)

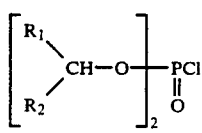 (6)

R$_2$ and R$_2$ being such as defined above.

The groups hereinafter mentioned illustrate particular products which can be employed within the scope of the present invention.

It is thus possible to start from saturated aliphatic alcohols, more particularly primary and secondary alcohols, such as 1-butanol, 1-octanol, 2-pentanol and 2-octanol.

It is also possible to use primary or secondary ethylenic alcohols, especially allyl alcohols.

The process of the invention can similarly be employed with acid alcohols and especially with lactic acids or lactates.

As already seen above, the invention also applies to products containing a heterocyclic ring, this heterocyclic ring containing one or more heteroatoms selected from oxygen, sulfur or nitrogen.

It is thus possible to start from products of formula (1) in which at least one of R$_1$ and R$_2$ is a heterocyclic ring of the furan or pyran type, such as products of the formulae:

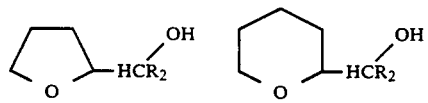

it being possible for R$_2$ to be hydrogen in particular. 2-Hydroxymethyltetrahydropyran and 2-hydroxymethyltetrahydrofuran are particularly suitable.

All that has been said here on the subject of the starting alcohols and particularly with respect to R$_1$ and R$_2$ is obviously applicable to all the corresponding or analogous compounds of formulae (3), (4), (5) and (6).

It is important to note that the process of the invention is particularly advantageous insofar as it makes it possible to obtain optically active products.

If the starting material is optically active, the process of the present invention can produce a final product which is also optically active, although an inversion of configurations may occur.

The various stages of the process will now be described with more particularity.

As already seen above, the process of the invention can utilize starting materials of the formulae (3), (4), (5) and (6). These compounds may be prepared or obtained commercially beforehand. As an alternative, the compounds may be manufactured during the course of the process itself, such as is the case when starting from the corresponding alcohol.

In this latter case, the first part of the process consists in bringing the alcohol into contact with phosgene, thionyl chloride or phosphorus oxychloride, depending on whether it is intended to obtain the compounds of formula (3), (4), (5) or (6) respectively.

The reactants may be introduced in any order when this first part of the process is implemented.

Furthermore, the reaction may be carried out in bulk or in a solvent. If a solvent is used, an aprotic solvent is preferably employed.

Representative solvents include saturated hydrocarbons (n-pentane, 2-methylhexane, cyclohexane), aromatic hydrocarbons (benzene, toluene, ethylbenzene), saturated aliphatic or aromatic ketones, saturated aliphatic or aromatic halogenated hydrocarbons, and saturated aliphatic or aromatic esters. One or more solvents may be utilized.

Aromatic or other halogenated hydrocarbons are generally preferred solvents.

The reaction is generally conducted at a temperature ranging from 0° C. to that of reflux of the solvent where appropriate, and advantageously from 5° to 60° C.

If the reaction is carried out in the presence of a solvent, the dilution of the reaction product will be from 0.5% to 99% by weight relative to the total weight of the solution, and preferably from 5 to 50%.

The number of equivalents, relative to the alcohol, of POCl$_3$ will be a function of the intermediate of formula (5) or (6) which it is intended to prepare. It generally ranges from 0.4:1 to 3:1, and preferably from 0.4:1 to 1.1:1. The number of equivalents of SOCl$_2$ or COCl$_2$ generally ranges from 0.9:1 to 3:1, and more preferably from 0.9:1 to 1.1:1.

The second part of the process, in the case where the starting material is an alcohol, or the essential part of one of the embodiments of the process, if starting directly from at least one of the compounds of formula (3), (4), (5) or (6), comprises reacting with a brominating agent, either, in the second part, the reaction mixture or the reaction product resulting from the first part or, if starting directly with a compound of formula (3), (4), (5) or (6), at least one of the compounds (3), (4), (5) or (6).

Both inorganic and organic bromides may be used An acid bromide and an alkylammonium bromide are preferred brominating agents.

As defined herein, an acidic bromide is any compound based on bromine and capable of producing Br$^-$ ions in the reaction mixture. Exemplary acidic bromides include hydrobromic acid, alkali metal bromides, such as LiBr and NaBr, and hydrobromides of aliphatic or aromatic tertiary amines, such as trimethylamine, pyridine or picoline hydrobromide.

With regard to alkylammonium bromides, tetrabutylammonium bromide is preferred.

With regard to the reaction conditions (reaction in bulk or in a solvent, temperature, concentration, and the like), all that has been said above concerning the first part of the reaction applies here as well. The number of equivalents of brominating agent, relative to the chloroformate, chlorosulfite or chlorophosphite, usually lies in the range of 0.9:1 to 3:1.

At the end of the treatment with the brominating agent, the required brominated compound is obtained and can be collected or isolated from the reaction mixture by any known suitable means.

However, the invention comprises a number of preferred embodiments which can be employed to increase the yield of brominated product, especially in the case where the particular starting materials are less reactive than others. These preferred embodiments will be described below.

According to a first preferred embodiment, the reaction mixture or the reaction product resulting from the bromination stage is heated. The heating is carried out at a temperature which is generally at least 30° C. and more particularly at least 50° C. It is possible, however, for this temperature to be as high as that of the reflux of the solvent where appropriate. At the end of this heating stage, the brominated product may be isolated and collected by any known means.

According to a second preferred embodiment, the above-mentioned reaction mixture or product resulting from the bromination stage is brought into contact with a compound containing trisubstituted nitrogen, such as an amine selected from the group of aliphatic and aromatic tertiary amines and nitrogen-containing heterocyclic rings. Examples include trialkylamines, such as triethylamine, pyridine or picoline.

Other exemplary trisubstituted nitrogen compounds include amides or formamides like, for example, dimethylformamide or dimethylacetamide.

It is also possible to employ as the trisubstituted nitrogen compound urea derivatives such as ureas substituted with alkyl groups. For example, tetramethylurea may be employed.

As previously, the reaction may be conducted in bulk or in a solvent medium with a solvent of the same type as indicated above.

The compound containing trisubstituted nitrogen is usually employed in a catalytic quantity, for example, the number of equivalents, relative to the brominated compound, of this compound ranges from $0.1 \times 10^{-2}:1$ to 1:1; more particularly, from 0.01:1 to 0.1:1.

It is also possible to utilize heating during this stage of contact with the compound containing trisubstituted nitrogen. For example, a temperature ranging from 30° C. to the temperature of reflux of the solvent can e used.

At the end of this stage wherein the trisubstituted nitrogen is introduced, the brominated product may be isolated and collected by any known means.

Lastly, a final embodiment of the invention consists, as has been seen above, in reacting the brominating agent with a reactant chosen from thionyl chloride, phosgene and phosphorus oxychloride.

Then, the reaction product thus obtained is subsequently brought into contact with a compound, such as an alcohol, to be brominated, for example by running the alcohol into the reaction mixture obtained in the preceding step.

It should be noted that this variant applies more particularly to the case of thionyl chloride.

Otherwise, at the end of the alcohol reaction step, the various other methods of carrying out the invention which have been described above can be implemented. For example, it is possible to heat the product or the reaction mixture obtained. It is also possible to react, with or without heating, the product or the reaction mixture obtained with a trisubstituted nitrogen compound.

All of the information about reactants and operating conditions previously stated apply to each of the steps of this final embodiment.

Other preferred forms of the invention can, furthermore, be envisaged. Thus, in the case of the use of a compound containing trisubstituted nitrogen, the above-mentioned stages may be reversed, that is to say the chloroformate, chlorosulfite or chlorophosphite may first be contacted with the compound containing trisubstituted nitrogen, followed by contact with the brominating agent.

It should be noted that the two stages can even be combined into a single stage. Specifically, the compound containing tri-substituted nitrogen and the brominating agent can be introduced simultaneously or immediately following each other.

All that has been stated above on the subject of the operating conditions in the case of each of the stages (presence or absence of a solvent, temperature, concentration, etc.) also applies here in the case of these two latter alternative forms of utilizing the compound containing trisubstituted nitrogen.

It should be noted, however, that in the case of the combination of brominating agent and compound containing trisubstituted nitrogen in a single stage, it is preferable to employ hydrobromides which act as both the brominating agent and the compound containing trisubstituted nitrogen. In such a case, the hydrobromides are employed in stoichiometric rather than catalytic quantities.

Concrete examples of the invention will now be given. The examples are illustrative only and do not limit the invention.

EXAMPLE 1

This example concerns the preparation of 2-bromomethyltetrahydropyran.

20.2 g (0.165 mol) of thionyl chloride are charged into a four-necked 250-ml flask equipped with a vertical condenser supporting a hydrogenation head, connected to a bubbler and to an HCl trap, a 25-ml dropping funnel, a thermometer and a gas inlet connected to a bottle of HBr (sulfuric acid trap and a retaining flask).

17.4 g (0.15 mol) of 2-hydroxymethyltetrahydropyran are then added over 1 h 30 min while a temperature of approximately 20°-25° C. is maintained in the reaction mass. The release of HCl, which begins as soon as the alcohol is added, stops approximately 20 minutes after the end of addition. An orange-colored solution is then obtained.

13.35 g (0.165 mol) of HBr gas are then introduced into the reaction mass at a temperature ranging from 25° to 30° C. over 1 h 30 min. A new release of HCl takes place.

1.5 g (0.015 mol) of triethylamine are then added quickly, and the reaction mixture is heated to a temperature of 70° C. During the first three hours of heating, a slow release of $SO_2$ is observed.

After an additional two hours of heating, the reaction mass is cooled. After dilution with methylene chloride, the mixture is washed until neutral with water and a saturated solution of sodium bicarbonate, and is then dried and concentrated. 25.9 g of a black viscous oil are thus obtained.

After the removal of tar by distillation (75°–79° C. at 17 mm Hg), 21.5 g of a colorless liquid are obtained, estimated by titration to contain 94% of 2-bromomethyltetrahydropyran (yield=75.3%).

EXAMPLE 2

This example concerns the preparation of S(−)-methyl bromopropionate.

15 g (0.126 mol) of thionyl chloride and 25 ml of methylene chloride are charged into a 100-ml reactor equipped in the same manner as the four-necked flask of Example 1.

10.9 g (0.105 mol) of methyl D-lactate (D/(L+D)=96.9%) are then added over one hour and at 25° C. and a release of HCl is observed. 9.6 g (0.12 mol) of HBr gas are then introduced over one hour and at ambient temperature. A new release of HCl takes place.

85 μl of pyridine (0.001 mol) ar then introduced and the mixture is heated under reflux for 8 hours 40 min.

After the reaction mixture has cooled to ambient temperature, 77.4% of the methyl bromopropionate and 9% of the corresponding chloro derivative are determined by gas phase chromatography (dichlorobenzene reference).

After a conventional treatment of the reaction mixture (aqueous washings, extraction with methylene chloride, drying, filtration and concentration), the crude reaction product is distilled (45°, 17 mbar) to produce S(−) methyl bromopropionate.

The inversion of configuration has been produced in a 98% yield, as confirmed by GPC analysis on a chiral column (D/L+D) of the bromopropionate =4.3%).

Enantiomeric yield: 98%.

EXAMPLE 3

This example concerns the preparation of 2-bromooctane.

13.02 g (0.1 mol) of 2-octane-2-ol are added over 1 hour to thionyl chloride (13.09 g; 0.11 mol) maintained at 10° C. After 25 min with stirring and purging with argon to expel the HCl released, 8.8 g (0.11 mol) of HBr gas are added over 1 hour at 10° C.

Triethylamine (1 g; 0.01 mol) is then added at 5° C. and the reaction mixture is then allowed to return to ambient temperature. A heat release (35° C.) and a strong release of gas are observed. Stirring is continued for 1 hour at 35° C.

After conventional treatment, 12.44 g of crude reaction product are recovered and analyzed by titration for 75% of the expected bromo product (yield =48%).

EXAMPLE 4

This example concerns the preparation of allyl bromide.

Allyl alcohol (5.80 g; 0.1 mol) is added over 45 min to 13.09 g (0.11 mol) of thionyl chloride cooled to 10° C. After 45 min of stirring, 8.8 g of HBr gas are added to the reaction mixture, which is maintained at a temperature of 10° C. (addition time: 1 hour 10 minutes).

The mixture is stirred for 1 hour and is then purged with argon to expel the HCl released. It then appears that allyl bromide has formed spontaneously.

EXAMPLE 5

This example describes another synthesis of methyl S-bromopropionate.

10 g (54 mmol) of methyl D-lactate chlorosulfite (analysis of the lactate as D enantiomer: 96.7%) are charged into a 50-ml four-necked flask equipped with a vertical condenser supporting a hydrogenation head connected to a bubbler and to an HCl trap, a thermometer and a gas inlet connected to a bottle of HBr.

5.6 g of gaseous HBr (69 mmol) are then introduced over 1 hour 10 minutes and at 30° C. in the reaction mixture, and the reaction mixture is then heated to 100° C. for 6 h 05 min.

Quantitative analysis of the crude reaction product using gas phase chromatography shows that the mixture contains 6.75 g of bromopropionate, representing a 75% yield.

The reaction mixture is then taken up with 30 ml of $CH_2Cl_2$, is washed with 6×30 ml of water, is dried over $Na_2SO_4$ and the solvent is evaporated off.

Analysis of the bromopropionate obtained using chiral VPC shows that it contains 93.9% of the L- enantiomer, representing an enantiomeric yield of 94%.

EXAMPLE 6

This example concerns the synthesis of methyl S-bromopropionate from methyl D-lactate chlorosulfite.

10.01 g of methyl D-lactate chlorosulfite (0.054 mol) and 43 microliters of pyridine (0.53 mmol) are charged into the same 50-ml four-necked flask as in Example 5. 4.9 g of gaseous HBr (0.060 mol) are then introduced into the reaction mixture over 1 hour while the temperature is maintained from 25° to 30° C. The reaction mixture is then maintained at ambient temperature for 15 min and is heated to 80° C. for 1 hour and is then cooled.

VPC analysis of the crude reaction product shows that it contains 8.59 g of bromopropionate, representing a 95.6% yield.

The crude reaction product is then taken up with 30 ml of $CH_2Cl_2$, is washed with water until neutral; the product is dried under $Na_2SO_4$, and the solvent is evaporated off.

Chiral VPC analysis of the product obtained shows that the bromopropionate obtained contains 92.4% of the S(−) enantiomer, representing an enantiomeric yield of 91%.

EXAMPLE 7

9.97 g of methyl D-lactate chlorosulfite (53.4 mmol) are charged into a 25-ml three-necked flask equipped in the same way as that of Example 5. 4.7 g of HBr gas are then introduced over 50 min while the temperature is maintained between 25° and 30° C. 43 microliters of pyridine (0.54 mmol) are then added and the reaction mixture is heated to 80° C. for 35 min.

VPC analysis of the crude reaction product shows that it contains 8.24 g of bromopropionate, representing a 92.4% yield.

Chiral PPC analysis of the crude product shows that the bromopropionate obtained contains 94.6% of S(−)bromopropionate, representing an enantiomeric yield of 95%.

What we claim is:

1. A process for the bromination of an alcohol, comprising the steps of:

(1) contacting an alcohol having the formula (1)

wherein $R_1$ and $R_2$ may be identical or different and are selected from the group consisting of a heterocyclic ring containing at least one heteroatom selected from oxygen, sulfur and nitrogen, a hydrogen atom, an alkyl, alkenyl or alkynyl radical, said alkyl, alkenyl or alkynyl radical being linear or branched, an unsubstituted or substituted aryl radical, and a cycloalkyl, alkylcycloalkyl, terpene, $-CO_2R_3$, $-(CH_2)_n-CO_2R_3$, $-COR_3$, $-SOR_3$ or $-SO_2R_3$ radical, n being an integer, and $R_3$ being selected from the group consisting of a hydrogen atom or an alkyl, alkenyl or alkynyl radical, said alkyl, alkenyl or alkynyl radical being linear or branched, with the proviso that $R_3$ cannot be a hydrogen atom in the $-SOR_3$ or $-SO_2R_3$ moiety with at least one reactant selected from thionyl chloride, phosgene and phosphorus oxychloride for a time sufficient to form at least one reaction product selected from a chloroformate, a chlorosulfite and a chlorophosphite; and (2) contacting said at least one reaction product with a brominating agent for a time sufficient to brominate said at least one reaction product at a temperature which does not decompose the brominated reaction product.

2. The process of claim 1, further comprising the additional step of subsequently heating said brominated reaction product obtained in step (2).

3. The process of claim 1, further comprising the additional step of subsequently contacting said brominated reaction product obtained in step (2) with a compound containing a tri-substituted nitrogen.

4. The process of claim 1, further comprising the additional step of prior to step (2) and after step (1), contacting said at least one reaction product selected from the group consisting of a chloroformate, a chlorosulfite and a chlorophosphite with a compound containing a trisubstituted nitrogen.

5. The process of claim 1, wherein in step (2) said at least one reaction product is simultaneously contacted with said brominating agent and a compound containing a trisubstituted nitrogen.

6. The process of claim 1, wherein said alcohol is a primary or secondary alcohol.

7. The process of claim 3, wherein said compound containing a trisubstituted nitrogen is selected from the group consisting of aliphatic and aromatic tertiary amines, nitrogen containing heterocyclic amides, formamides, and a urea derivative.

8. The process of claim 1, wherein at least one of $R_1$ and $R_2$ is a heterocyclic ring of the furan or pyran type.

9. The process of claim 1, wherein said alcohol is selected from the group consisting of a primary or secondary saturated alcohol, a primary or secondary ethylenic alcohol, and a primary or secondary acid alcohol.

10. The process of claim 9, wherein said acid alcohol is selected from the group consisting of lactic acid and lactates.

11. The process of claim 1, wherein at least one of said steps (1) and (2) is carried out in bulk.

12. The process of claim 1, wherein at least one of steps (1) and (2) is carried out in the presence of a solvent.

13. The process of claim 1, wherein said brominating agent is an acidic bromide.

14. The process of claim 13, wherein said acidic bromide is selected from the group consisting of hydrobromic acid, alkali metal bromides and the hydrobromides of aliphatic or aromatic tertiary amines.

15. The process of claim 1, wherein said brominating agent is an alkyl ammonium bromide.

* * * * *